(12) United States Patent
Schaeffer et al.

(10) Patent No.: US 10,492,865 B2
(45) Date of Patent: Dec. 3, 2019

(54) SUCTION LITHOTRIPSY APPARATUS, METHOD AND KIT

(71) Applicant: Cook Medical Technologies LLC, Bloomington, IN (US)

(72) Inventors: Darin Schaeffer, Bloomington, IN (US); Nicholas Hardert, Cincinnati, OH (US); Thomas Cherry, Covington, LA (US)

(73) Assignee: Cook Medical Technologies LLC, Bloomington, IN (US)

( * ) Notice: Subject to any disclaimer, the term of this patent is extended or adjusted under 35 U.S.C. 154(b) by 296 days.

(21) Appl. No.: 15/722,137

(22) Filed: Oct. 2, 2017

(65) Prior Publication Data

US 2018/0021091 A1 Jan. 25, 2018

Related U.S. Application Data

(63) Continuation of application No. 13/606,323, filed on Sep. 7, 2012, now Pat. No. 9,775,764.

(60) Provisional application No. 61/533,191, filed on Sep. 10, 2011.

(51) Int. Cl.
| | | |
|---|---|---|
| *A61B 18/26* | (2006.01) | |
| *A61B 17/22* | (2006.01) | |
| *A61B 17/34* | (2006.01) | |

(52) U.S. Cl.
CPC .............. *A61B 18/26* (2013.01); *A61B 17/22* (2013.01); *A61B 17/22012* (2013.01); *A61B 17/3421* (2013.01); *A61B 17/3462* (2013.01); *A61B 2017/22084* (2013.01); *A61B 2217/005* (2013.01); *A61B 2217/007* (2013.01)

(58) Field of Classification Search
CPC .............. A61B 17/22; A61B 17/22012; A61B 2217/005; A61B 2217/007; A61B 18/26; A61B 2017/22084
See application file for complete search history.

(56) References Cited

U.S. PATENT DOCUMENTS

| | | |
|---|---|---|
| 4,867,141 A | 9/1989 | Nakada et al. |
| 5,211,625 A | 5/1993 | Sakurai et al. |
| 5,290,294 A | 3/1994 | Cox et al. |
| 5,944,687 A | 8/1999 | Benett et al. |
| 6,375,651 B2 | 4/2002 | Grasso et al. |
| 6,527,704 B1 | 3/2003 | Chang et al. |
| 6,936,025 B1 | 8/2005 | Evans et al. |
| 8,419,783 B2 | 4/2013 | Frye et al. |
| 9,775,674 B2 | 10/2017 | Schaeffer et al. |
| 2005/0143678 A1 | 6/2005 | Schwarz et al. |

(Continued)

FOREIGN PATENT DOCUMENTS

| | | |
|---|---|---|
| WO | 2004096061 | 11/2004 |
| WO | 2013036732 | 3/2013 |

OTHER PUBLICATIONS

European Patent Office, "Communication pursuant to Article 94(3) EPC," application No. 12762140.7, dated Nov. 14, 2017.

(Continued)

*Primary Examiner* — Anh T Dang
(74) *Attorney, Agent, or Firm* — Buchanan Van Tuinen LLC

(57) ABSTRACT

Medical devices, methods and kits useful in the disruption and removal of unwanted materials, such as calculi and other formations, from within body lumens are described. The disclosure describes particular embodiments and methods useful in the lithotriptic removal of stones from the salivary glands.

20 Claims, 7 Drawing Sheets

(56) References Cited

U.S. PATENT DOCUMENTS

2007/0213765 A1 9/2007 Adams et al.
2013/0237967 A1 9/2013 Schaeffer et al.

OTHER PUBLICATIONS

International Searching Authority, International Application No. PCT/US2012/054105; Notification of Transmittal of the International Search Report and the Written Opinion, dated Dec. 7, 2012, p. 1-14.
European Patent Office, Examination Report from European Application 12762140.7; dated Apr. 4, 2017.
International Bureau of WIPO, International Preliminary Report on Patentability and Written Opinion, for International Application No. PCT/US2012/054105. dated Mar. 20, 2014. p. 1-9.

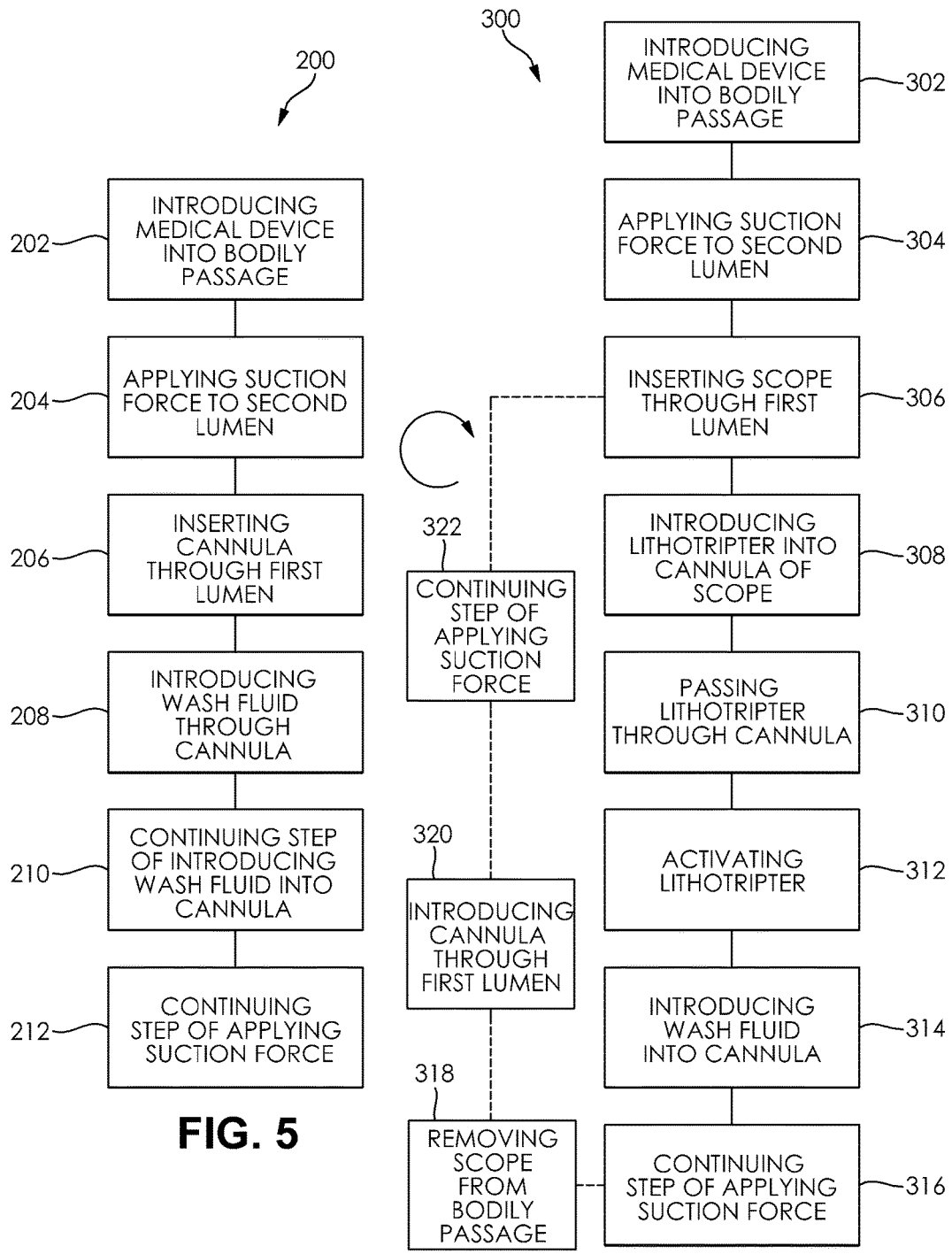

SUCTION LITHOTRIPSY APPARATUS, METHOD AND KIT

CROSS REFERENCE TO RELATED APPLICATIONS

This application is a continuation of U.S. patent application Ser. No. 13/606,323, filed on Sep. 7, 2012, and which claims the benefit of U.S. Provisional Application Ser. No. 61/533,191, filed on Sep. 10, 2011. The entire contents of each of these related applications is incorporated into this disclosure by reference.

FIELD

The disclosure relates generally to the field of medical devices. More particularly, the disclosure relates to medical devices, methods and kits useful in the disruption and removal of unwanted materials, such as calculi and other formations, from within body lumens. The disclosure describes particular embodiments and methods useful in the lithotriptic removal of stones from the salivary glands.

BACKGROUND

The treatment of various medical conditions related to the salivary ducts can involve several techniques, including wire insertion, dilation of the papilla and duct, sheath insertion, irrigation, visualization, balloon dilatation of strictures, lithotripsy, and stone removal. In the salivary duct, each of these procedures is complicated by the size of the duct itself, which is relatively small in comparison to other body vessels within which minimally invasive procedures have become common, such as the vessels of the vasculature system. Lithotripsy procedures can be particularly challenging in these relatively small ducts because of the need for removal of stone fragments from the duct following disruption of the stone.

While the use of a suction force can aid in the removal of stone fragments during a lithotripsy procedure, its use in the salivary ducts risks collapse of the duct structure due to the relative small size. The art lacks an adequate device that allows for the use of suction during lithotripsy procedures while addressing this unique challenge presented by these ducts.

Thus, a need exists for improved lithotripsy devices, methods and kits that are particularly well-suited for use in the salivary ducts and other small body vessels.

BRIEF SUMMARY

Various exemplary methods are described and illustrated herein.

An exemplary method of removing an impediment in a body vessel of a patient comprises introducing a medical device having a proximal end and a distal end into said body vessel such that the distal end of the medical device is disposed within said body vessel. The medical device defines a first lumen that extends along a first axis and a second lumen in fluid communication with the first lumen and that extends along a second axis disposed at an angle to the first axis. The first lumen has a proximal opening disposed at the proximal end of the medical device and a distal opening disposed at the distal end of the medical device. Another step comprises applying a suction force to the second lumen such that air from the environment external to said body vessel is pulled into the first lumen and through the second lumen. Another step comprises introducing a cannula having a proximal end and a distal end through the proximal opening of the first lumen such that the distal end of the cannula is disposed distal to the second lumen. Another step comprises introducing a wash fluid through the cannula such that the wash fluid exits the distal end of the cannula into said body vessel. Another step comprises continuing the step of introducing the wash fluid through the cannula until the wash fluid rises within the first lumen to a level sufficient for the suction force to pull the wash fluid into the second lumen. Another step comprises after the wash fluid achieves a level within the first lumen sufficient for the suction force to pull the wash fluid into the second lumen, continuing the step of applying a suction force to the second lumen such that the wash fluid is drawn through the second lumen.

Another exemplary method of removing an impediment in a body vessel of a patient comprises introducing a medical device having a proximal end and a distal end into said body vessel such that the distal end of the medical device is disposed within said body vessel. The medical device comprising a pass-through fitting, a first sheath, and a second sheath. The pass-through fitting defines a main body and a side arm. The main body has a first inner wall that defines a first lumen that extends along a first axis and the side arm has a second inner wall that defines a second lumen in fluid communication with the first lumen and that extends along a second axis disposed at an angle to the first axis. The first lumen has a proximal opening disposed at the proximal end of the medical device and a distal opening disposed at the distal end of the medical device. The first sheath is connected to the main body and is in fluid communication with the first lumen. The second sheath is attached to the side arm and is in fluid communication with the second lumen. Another step comprises applying a suction force to the second lumen such that air from the environment external to said body vessel is pulled into the first lumen and through the second lumen. Another step comprises introducing a cannula having a proximal end and a distal end through the proximal opening of the first lumen such that the distal end of the cannula is disposed distal to the second lumen. Another step comprises introducing a wash fluid through the cannula such that the wash fluid exits the distal end of the cannula into said body vessel. Another step comprises continuing the step of introducing the wash fluid through the cannula until the wash fluid rises within the first lumen to a level sufficient for the suction force to pull the wash fluid into the second lumen. Another step comprises after the wash fluid rises within the first lumen to a level sufficient for the suction force to pull the wash fluid into the second lumen, continuing the step of applying a suction force to the second lumen such that the wash fluid is drawn through the second lumen.

Various exemplary medical devices are also described and illustrated herein.

An exemplary medical device comprises a pass-through fitting, a first sheath, a second sheath, and a cannula. The pass-through fitting defines a main body and a side arm. The main body has a proximal end, a distal end, and a first inner wall that defines a first lumen that extends along a first axis. The side arm has a second inner wall that defines a second lumen in fluid communication with the first lumen and that extends along a second axis disposed at angle to the first axis. The first lumen has a proximal opening disposed at the proximal end of the main body and a distal opening disposed at the distal end of the main body. The first sheath is connected to the main body and is in fluid communication with the first lumen. The second sheath is connected to the side arm and is in fluid communication with the second lumen. The cannula has a proximal end and a distal end disposed through the proximal opening of the first lumen such that the distal end of the cannula is disposed distal to the second lumen and a first fluid path is formed between the first inner wall and the cannula. A wash fluid passed through the proximal end of the cannula exits the distal end of the cannula. A suction force applied to the second lumen pulls the wash fluid exiting the distal end of the cannula into the second lumen or pulls fluid from the external environment through the proximal opening of the first lumen and into the second lumen.

Additional understanding of these exemplary medical devices and methods can be obtained with review of the detailed description, below, and the appended drawings.

BRIEF DESCRIPTION OF THE DRAWINGS

FIG. 5 is a flowchart illustration of a method of performing lithotripsy.

FIG. 6 is a flowchart illustration of a second method of performing lithotripsy.

DETAILED DESCRIPTION

Figure 1:
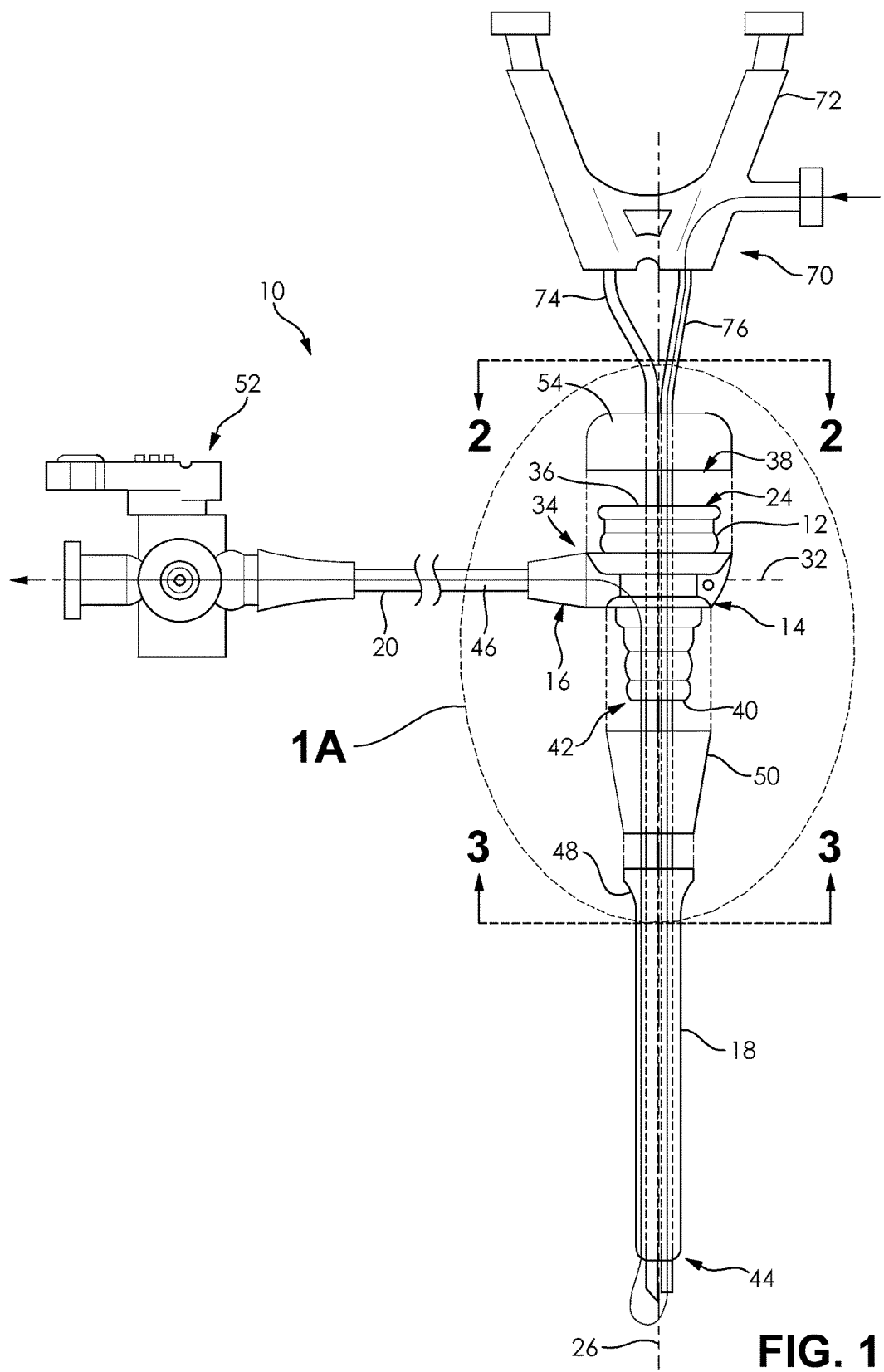
FIG. 1 is an exploded view of a first exemplary medical device.
Figure 1A:
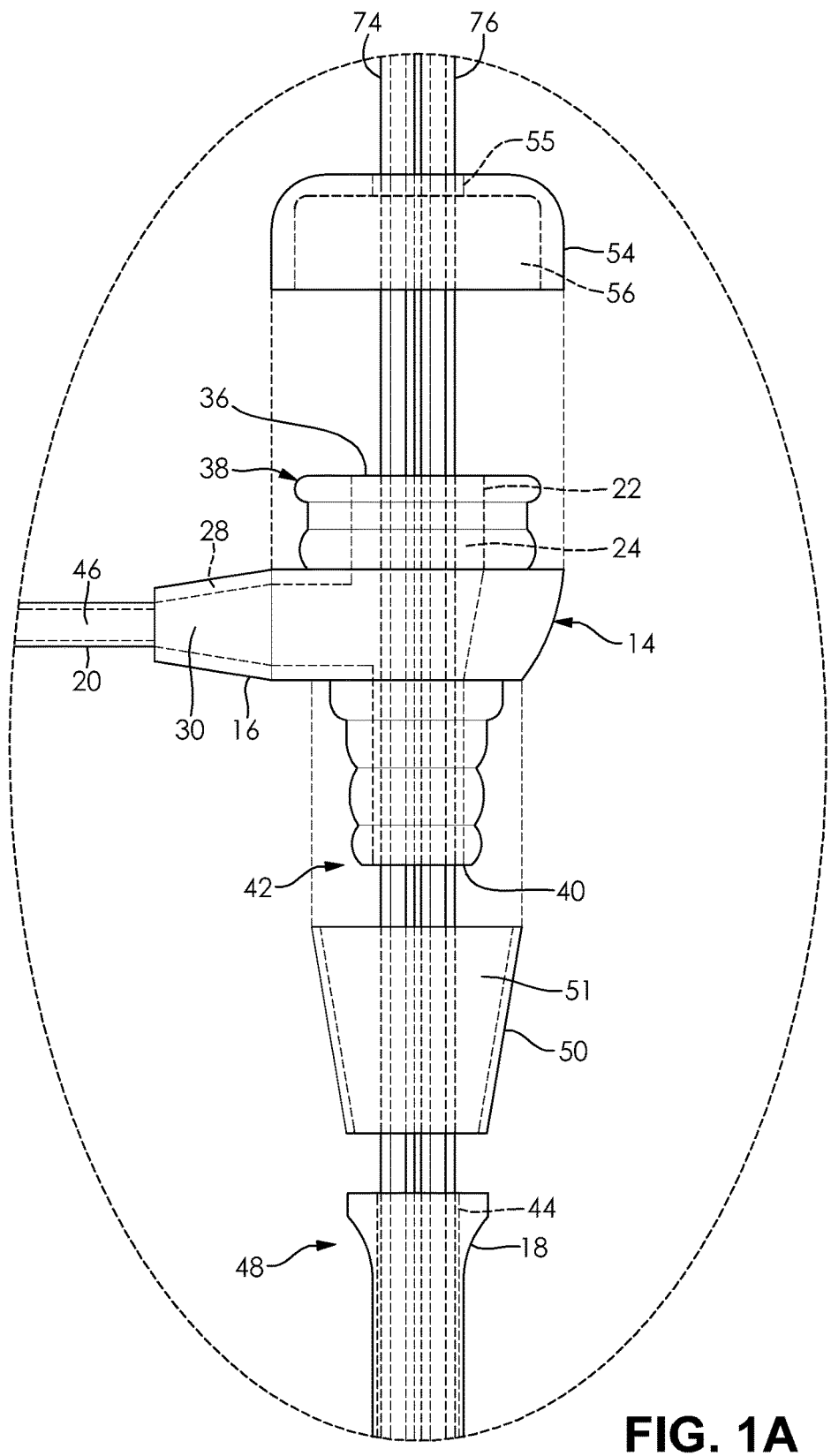
FIG. 1A is a magnified view of the area indicated in FIG. 1.
Figure 2:
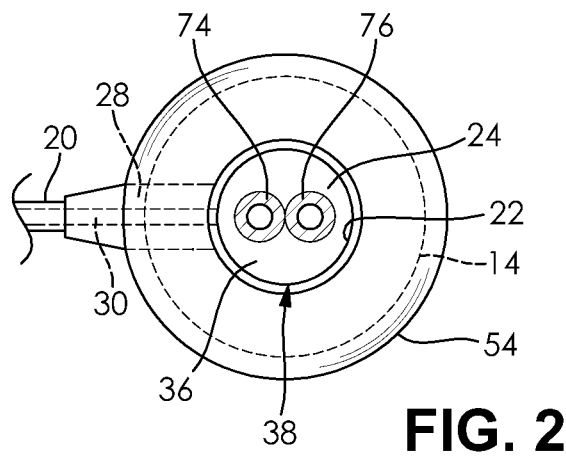
FIG. 2 is a sectional view of the medical device illustrated in FIG. 1, taken along line 2-2.
Figure 3:
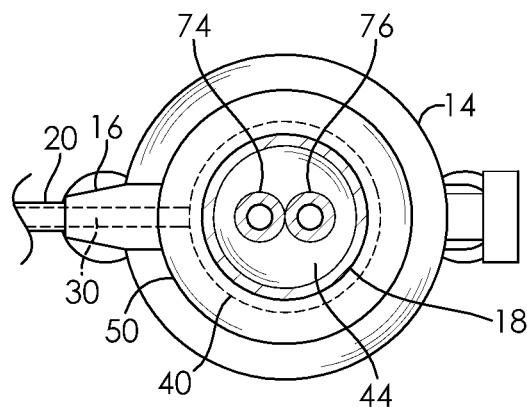
FIG. 3 is a sectional view of the medical device illustrated in FIG. 1, taken along line 3-3.

The following detailed description and the appended drawings describe and illustrate various exemplary demonstration apparatuses, kits and methods. The description and drawings are exemplary in nature and are provided to enable one skilled in the art to make and use one or more exemplary apparatus, kit and/or to practice one or more exemplary method. They are not intended to limit the scope of the claims in any manner.

FIGS. 1, 1A, 2, 3, 4A, 4B, and 4C illustrate an exemplary medical device 10. The medical device 10 includes a pass-through fitting 12 defining a main body 14 and a side arm 16. A first sheath 18 is attached to the main body 14 and a second sheath 20 is attached to the side arm 16. In the illustrated embodiment, an optional scope 70 comprising a handle 72 and first 74 and second 76 cannula is associated with the medical device 10. The scope has a proximal end at, or near, handle 72 and a distal end at the end of the cannula opposite that connected to the handle. Thus, the cannula extends from the handle to the distal end of the scope.

The main body 14 has a first inner wall 22 that defines a first lumen 24 extending along a first axis 26 of the medical device 10. Similarly, the side arm 16 has a second inner wall 28 that defines a second lumen 30 that extends along a second axis 32 of the medical device 10. The second axis 32 is disposed at an angle to the first axis 26. That is, the second axis 32 intersects the first axis 26. The axes 26, 32 can be disposed at any suitable angle, and a skilled artisan will be able to select an appropriate angle for a medical device according to a particular embodiment based on various considerations, including the nature of the body vessel within which the medical device is intended to be used. A structure in which the axes 26, 32 lie on the same plane and intersect at a substantially orthogonally is considered suitable. Additional example angles considered suitable for a second axis to intersect a first axis include, but are not limited to, a 45 degree angle, a substantially 45 degree angle, any angle between 0 degrees and 45 degrees, any angle between 45 degrees and 90 degrees, a 90 degree angle, a substantially 90 degree angle, 135 degree angle, a substantially 135 degree angle, any angle between 135 degrees and 180 degrees, and any other angle considered suitable for a particular application.

While one side arm 16 has been illustrated and described, pass-through fitting 12 can define any suitable number of side arms, and skilled artisans will be able to select a suitable number of side arms for a pass-through fitting to define according to a particular embodiment based on various considerations, including the procedure intended to be performed. Example number of side arms considered suitable for a pass-through fitting to define include, but are not limited to, one, at least one, two, a plurality, three, four, and any other number considered suitable for a particular application.

The first 24 and second 30 lumens are in fluid communication with each other to define a branched flow path 34 through the pass-through fitting 12. The branched flow path 34 defines two paths along which fluid can flow through the main body 14 and into the side arm 16. For the first path, fluid flows through a proximal opening 36 defined by the proximal end 38, into the first lumen 24 and then into the second lumen 30. For the second path, fluid flows through a distal opening 40 defined by the distal end 42, into the first lumen 24 and then into the second lumen 30. For each flow path, fluid can also flow in the reverse direction.

The first sheath 18 defines a first sheath lumen 44 and the second sheath 20 defines a second sheath lumen 46. The first sheath 18 is attached to the main body 14 in any suitable manner such that the first sheath lumen 44 is in fluid communication with the first lumen 24 of the main body 14. Similarly, the second sheath 20 is attached to the side arm 16 in any suitable manner such that the second sheath lumen 46 is in fluid communication with the second lumen 30 of the side arm 16. With this arrangement, the sheaths 18, 20 further extend the branched flow path 34 defined by the first 24 and second 30 lumens of the pass-through fitting 12. The inner diameter of the first lumen 24, second lumen 30, and the second sheath lumen 46 may be greater than the inner diameter of the first sheath lumen 44 at the proximal end of the first sheath 18 to ensure fragments traveling through first sheath 18 can pass through first lumen 24, second lumen 30, and the second sheath lumen 46.

Each sheath 18, 20 can be attached to the pass-through fitting 12 in any suitable manner, such as by adhesives, mechanical connectors, clamps, and any other suitable structure or component for attaching a sheath to a fitting. Furthermore, one or both of the sheaths 18, 20 can define additional structure that facilitates its attachment to the pass-through fitting. For example, as best illustrated in FIG. 1, the first sheath 18 can define a flared proximal end 48 that facilitates its attachment to the pass-through fitting 12. In this embodiment, a locking connector 50 that defines a locking connector lumen 51 can be placed over the flared proximal end 48 to secure the first sheath 18 to the pass-through fitting 12. The locking connector 50 can define threads or other suitable structure that mates with complimentary structure on the pass-through fitting to for a connection that holds the first sheath 18 in a captive position.

In use, a suction force applied to the second lumen 30 of the side arm 16 pulls fluid from the first lumen 24 of the main body 14 and into the second lumen 30. With the attached sheaths 18, 20, a suction force applied to the second sheath lumen 46 of the second sheath 20 is able to pull fluid that has reached the point in the first lumen 24 of the main body 14 that intersects with the second lumen 30, such as fluid that has been forced upward through the first sheath lumen 44 as a result of pressure build up from continued introduction of fluid into a blind body vessel of limited elasticity, as described more fully below. Once this fluid level is achieved, the fluid enters the second lumen 30 of the side arm 16, and eventually into the second sheath lumen 46. Because of the branched flow path 34, fluid can also enter the first lumen of the main body 14 through the opening 36 defined by the proximal end 38 of the main body 14. As described more fully below, these alternate routes of entry into the first lumen 24 enable the medical device 10 to apply a suction force during a lithotripsy procedure in a controlled manner.

The medical device 10 can include various additional components, such as a valve 52 attached to the second sheath 20. The valve 52 offers a control for selectively establishing fluid communication between the second sheath lumen 46 and a downstream component, such as a source of a suction force. If included, the valve 52 can be a part of a larger fitting that defines additional structure. For example, a valve fitting that includes additional ports can be included. In this embodiment, the valve is adapted to selectively establish fluid communication between the second sheath lumen 46 and one of its multiple ports.

As illustrated in FIG. 1, a proximal cap member 54 can be attached to the main body 14. If included, the proximal cap member 54 can be attached in any suitable manner, such as with an adhesive, a mechanical structural connection such as mating threads or a snap fit, or other suitable means for connecting two structures. Also, the proximal cap member 54 should define an opening 55 and lumen 56 that provide fluid access to the opening 36 defined by the main body 14. As such, the inclusion of the proximal cap member 54 doesn't eliminate the branched flow path 34.

A valve can be attached to the proximal cap member 54 and adapted to block fluid flow from the external environment into the first lumen 24. Any suitable valve can be used for valve 52 and/or the valve attached to the proximal cap member 54. Skilled artisans will be able to select a suitable valve according to a particular embodiment based on various considerations, including the treatment desired to be performed.

Advantageously, a device used with the medical device 10, such as scope 70, defines structure that allows it or a portion of it to be extended through the first lumen 24 in a manner that does not block fluid flow from the external environment into the first lumen 24. For example, as illustrated in FIG. 1, the first 74 and second 76 cannula of scope 70 can be extended through the first lumen 24 of the pass-through fitting 12 and into the first sheath lumen 44 without forming a seal or other block to fluid flow into the opening 36 of the pass-through fitting 12 from the external environment. Each of the first 74 and second 76 cannula of scope 70 defines a lumen that extends along the length of the cannula. This structural arrangement allows the medical device 10 to define two paths along which fluid can flow through the main body 14 and into the side arm 16. While the illustrated scope 70 is considered suitable, its specific structure is not considered necessary, and any suitable scope can be used with the medical device 10 and in the methods and kits described herein. For example, while the illustrated scope 70 includes first 74 and second 76 cannula that are attached or bonded together, a unitary structure that defines two independent lumens could also be used (e.g., a cannula that defines more than one lumen).

While using a scope 70 with medical device 10 has been illustrated and described, any suitable medical device can be used with medical devices described herein, and skilled artisans will be able to select a suitable medical device to use with the medical devices described herein according to a particular embodiment based on various considerations, including the treatment desired to be performed. Example medical devices considered suitable to use with the medical devices described herein include, but are not limited to, probes, scopes, cutting tools, elongate tubular members, suction devices, irrigation devices, graspers, forceps, lithotripters, balloons, drills, lasers, baskets, and any other medical device considered suitable for a particular application.

The proximal opening of the first sheath 18 may have a larger inner diameter than the distal portion of the first sheath 18 to ensure that fluid is not drawn up from the distal lumen as devices are inserted into the first sheath 18. This ensures fluid is only drawn into the second lumen 30 when the fluid level in the first lumen 24 is forced up to the level of the second lumen 30. Similarly, the proximal portion of the first lumen 24 may have a larger inner diameter than the distal portion of the first lumen 24. In addition, the cross-sectional area of the second lumen 30 can be equal to, substantially equal to, or greater than, the cross-sectional area of the first lumen 24, or the cross-sectional open area of the first lumen 24 external to the medical device when the first lumen contains a medical device, such as scope 70. Alternatively, the inner diameter of the second lumen 30 can be equal to, substantially equal to, or greater than, the inner diameter of the first lumen 24. These structural features can be included separately or in combination with each other.

Additional structure can include the attachment of a tapered fitting which is connected to the opposite end of second sheath 20 than the end that is attached to the pass-through fitting 12. This tapered fitting can be inserted into a vacuum line to facilitate connection to the vacuum source.

Figure 4A:
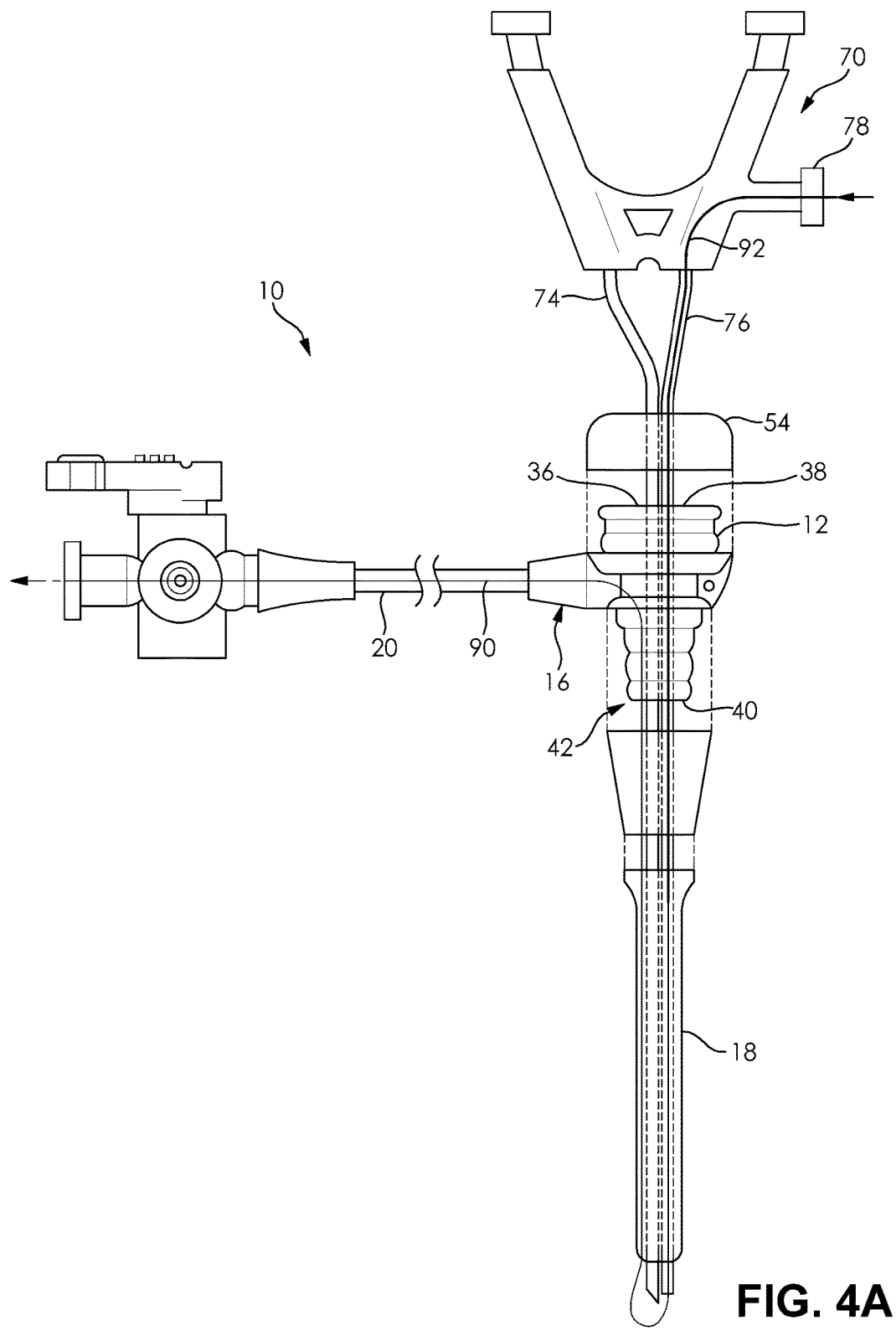
FIG. 4A is a side view of the medical device illustrated in FIG. 1, illustrating fluid flow through a fluid path of the device during a first stage of use.
Figure 4B:
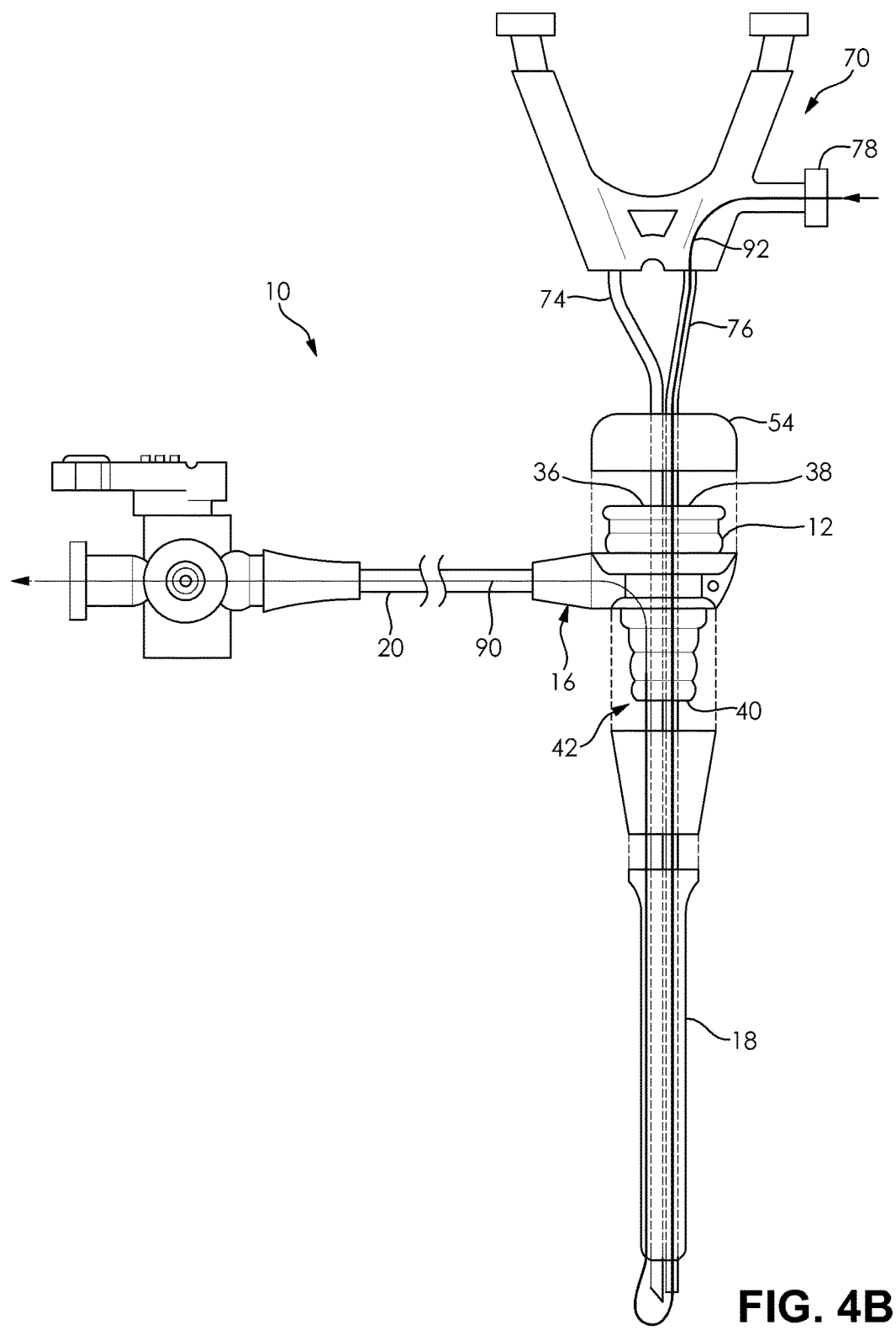
FIG. 4B is a side view of the medical device illustrated in FIG. 1, illustrating fluid flow through a fluid path of the device during a second stage of use.
Figure 4C:
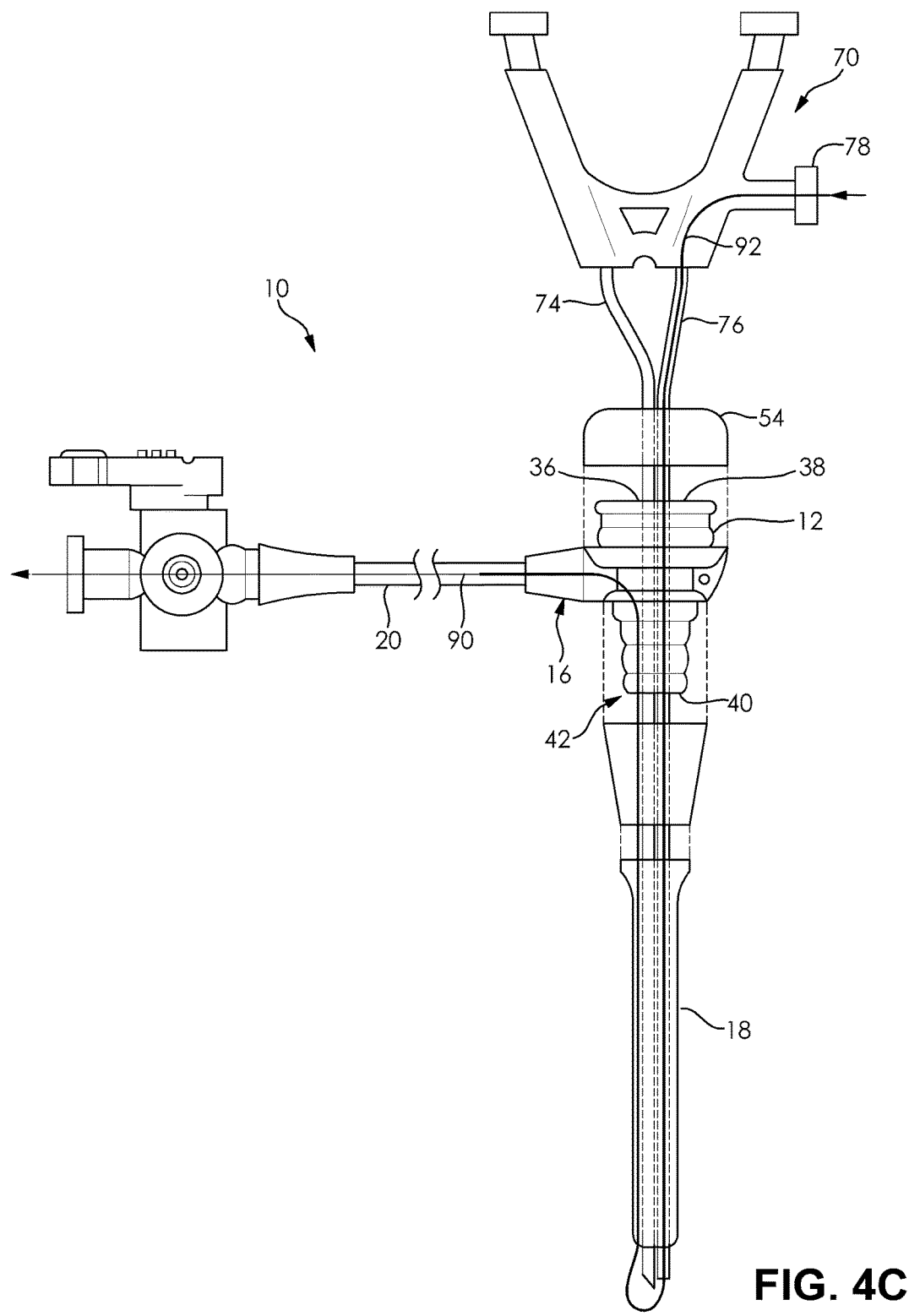
FIG. 4C is a side view of the medical device illustrated in FIG. 1, illustrating fluid flow through a fluid path of the device during a third stage of use.

FIGS. 4A, 4B, and 4C illustrate the medical device 10 in various stages of use, such as during performance of one of the methods described below. The figures illustrate the introduction of a wash fluid into the associated scope 70 and the travel of the flow of the fluid through a fluid path of the device 10 during the various stages of use. In each of the figures, the relatively light line 90 represents the overall fluid path and the relatively dark line 92 represents the portion of the fluid path along which fluid has flown at the illustrated stage of use.

FIG. 4A illustrates a first stage of use. In this stage, the wash fluid has been introduced into the scope 70 through a side port 78 that is in fluid communication with a cannula 76 (one of the two cannulae 74, 76 of the scope 70). Alternatively, if a cannula that defines more than one lumen is being used, the wash fluid can be introduced into one of the lumens defined by the cannula through a side port that is in fluid communication with the lumen. The pressure supplied by the continued introduction of the fluid into the side port 78 has forced the fluid along the fluid path 90, but the fluid has not yet exited the first sheath 18 attached to the pass-through fitting 12. At this stage, a suction force applied to the second sheath 20 draws air from the external environment through the opening 36 defined by the proximal end 38 of the main body 12, and through the opening defined by the proximal cap member 54. The air enters the first lumen 24 defined by the main body 14, and subsequently enters the second lumen 30 defined by the side arm 16. Ultimately, the air continues through the second sheath 20 toward the source of the suction force. This is possible because of the branched flow path 34 and prevents the suction force from being applied to the empty body vessel, which might otherwise damage the vessel or hinder visualization by the scope by inducing collapse.

FIG. 4B illustrates a second stage of use. In this stage, which follows the stage illustrated in FIG. 4A, the pressure supplied by the continued introduction of the fluid into the side port 78 has forced the fluid further along the fluid path 90. The fluid has exited the distal end of the first sheath 18 and entered the lumen defined by the body vessel. The blind nature of the salivary duct forces the fluid to re-enter the sheath 18 as it seeks the path of least resistance with continued introduction of fluid. The fluid has not, however, reached the second lumen 30 defined by the side arm 16. As a result, the suction force applied to the second sheath 20 continues to draw air from the external environment through the opening 36 defined by the proximal end 38 of the main body 12, and through the opening defined by the proximal cap member 54. As in the first stage illustrated in FIG. 4A, the air continues to enter the first lumen 24 defined by the main body 14, and continues to enter the second lumen 30 defined by the side arm 16. Ultimately, the air continues through the second sheath 20 toward the source of the suction force. Also similar to the first stage, the branched flow path 34 continues to prevent the suction force from being applied to the empty body vessel, which might otherwise damage the vessel by inducing collapse. In this stage, an impediment from the vessel, or fragments of an impediment, can travel with the fluid through the first sheath 18 external to the cannula 74, 76 of the scope 70. Alternatively, if a cannula that defines more than one lumen is being used, the impediment from the vessel, or fragments of an impediment, can travel with the fluid through the first sheath 18 external to the cannula.

FIG. 4C illustrates a third stage of use. In this stage, which follows the stage illustrated in FIG. 4B, the pressure supplied by the continued introduction of the fluid into the side port 78 has forced the fluid further along the fluid path 90. The fluid has reached the second lumen 30 defined by the side arm 16 in the pass-thorough fitting 12. As a result, the suction force applied to the second sheath 20 has begun to draw the fluid through the second lumen 30 of the side arm 16 and into the second sheath 20. In the pass-through fitting 12, the fluid has partially or completely sealed the second lumen 30 from the air entering the main body 14. In this stage, the suction pulls the fluid and impediments or fragments of an impediment through the second sheath 20, which can be collected as waste.

The medical devices are particularly well-suited for use in methods of removing impediments from body vessels. For example, the medical devices can be used in methods of performing lithotripsy in a salivary duct. For example, to fragment and/or remove a stone disposed within a salivary duct. The medical devices described herein can be used to treat any suitable body vessel and/or bodily passage, and skilled artisans will be able to select a suitable body vessel and/or bodily passage to treat using a medical device described herein based on various considerations, including the treatment intended to be performed. Example body vessels and/or bodily passages considered suitable include, but are not limited to, a salivary duct, urinary tract, and any other body vessel and/or bodily passage considered suitable for a particular embodiment.

Various methods of removing an impediment in a body vessel are provided. While the methods described herein are shown and described as a series of acts, it is to be understood and appreciated that the methods are not limited by the order of acts, as some acts may, in accordance with these methods, occur in different orders, and/or concurrently with other acts described herein.

FIG. 5 is a flowchart representation of a first exemplary method 200 of removing an impediment in a body vessel of a patient. This first exemplary method is useful for addressing impediments in body vessels that might be able to be removed without disruption of the structure of the impediment.

A first step 202 comprises introducing a medical device into the body vessel. The medical device is a medical device according to an embodiment of the invention, such as the medical device 10 illustrated in FIG. 1 and described above. Thus, a medical device can be introduced into the body vessel such that the distal end of the medical device, or the distal end of the first sheath, is disposed in the body vessel.

A second step 204 comprises applying a suction force to the second lumen of the medical device such that air from the environment external to the body vessel is pulled into the first lumen and through the second lumen.

A third step 206 comprises inserting a cannula having a proximal end and a distal end through the first lumen such that the distal end of the cannula is disposed distal to the second lumen. As described above, the cannula is inserted through the first lumen without forming a seal or otherwise blocking air or fluid flow into the first lumen from the external environment. An optional step comprises inserting a cannula having a proximal end and a distal end through the first lumen such that the distal end of the cannula is disposed distal to the distal end of the medical device.

A fourth step 208 comprises introducing a wash fluid through the cannula and into said body vessel such that the wash fluid exits the distal end of the cannula into said body vessel.

A fifth step 210 comprises continuing the step of introducing the wash fluid through the cannula until the wash fluid enters the first lumen to a level sufficient for the suction force to pull the wash fluid into the second lumen. Any level sufficient for the suction force to pull the wash fluid into the second lumen is considered suitable. Levels considered suitable include, but are not limited to, a level within the first lumen equal with the second lumen, a level within the first lumen along the diameter of the second lumen, a level within the first lumen and along the length of the first lumen, a level within the first lumen and disposed at the distal intersection between the first lumen and second lumen, a level within the first lumen and disposed at the proximal intersection between the first lumen and second lumen, and any other level considered suitable for a particular application.

A sixth step 212 comprises continuing the step of applying a suction force to the second lumen after the wash fluid achieves a level within the first lumen sufficient for the suction force to pull the wash fluid into the second lumen such that the wash fluid is drawn through the second lumen.

An optional step comprises removing the cannula from said body vessel by withdrawing the cannula through the first lumen such that the distal end of the cannula is disposed proximal to the proximal opening of the first lumen. Another optional step comprises removing the medical device from the body vessel such that the distal end of the medical device is free of the body vessel.

While various steps, alternative steps, and optional steps have been described above with respect to removing an impediment in a body vessel, these steps, alternative steps, and optional steps can be included in, accomplished concurrently with, and/or accomplished in the alternative to, the methodologies, steps, alternative steps, and/or optional steps described below with respect to the exemplary method 300 of removing an impediment in a body vessel.

FIG. 6 is a flowchart representation of another exemplary method 300 of removing an impediment in a body vessel of a patient. This exemplary method is useful for addressing impediments in body vessels that may require disruption of the structure of the impediment prior to removal from the body vessel.

A first step 302 comprises introducing a medical device into the body vessel. The medical device is a medical device according to an embodiment of the invention, such as the medical device 10 illustrated in FIG. 1 and described above. Thus, a medical device can be introduced into the body vessel such that the distal end of the medical device, or the distal end of the first sheath, is disposed in the body vessel.

Another step 304 comprises applying a suction force to the second lumen of the medical device such that air from the environment external to the body vessel is pulled into the first lumen and through the second lumen.

Another step 306 comprises inserting a scope having a handle and first and second cannula through the first lumen such that the distal end of each cannula extends axially beyond the second lumen in the body vessel. Alternatively, a cannula that defines more than one lumen can be used. Therefore, step 306 can comprise inserting a scope comprising a proximal end, a distal end, a handle, and a cannula extending from the handle to the distal end of the scope through the proximal opening of the first lumen such that the distal end of the scope is disposed distal to the second lumen. As described above, the cannula is inserted through the first lumen without forming a seal or otherwise blocking fluid flow into the first lumen from the external environment. An optional step comprises inserting a scope comprising a proximal end, a distal end, a handle, and a cannula extending from the handle to the distal end of the scope through the proximal opening of the first lumen such that the distal end of the scope is disposed distal to the distal end of the medical device.

Another step 308 comprises introducing a lithotripter into one of the cannulae of the scope. Alternatively, a cannula that defines more than one lumen can be used. Therefore, step 308 can comprise introducing a lithotripter having a proximal end and a distal end into a cannula. Any suitable lithotripter can be used, including a laser lithotripter, an ultrasonic lithotripter, and a pneumatic lithotripter.

Another step 310 comprises passing the lithotripter through the cannula until a distal end of the lithotripter is disposed in the body vessel at an effective distance from the impediment to be removed from the body vessel. The effective distance should be selected based on the type of lithotripter being used, and may include direct contact between the lithotripter and the impediment, which is considered an effective distance for a pneumatic lithotripter, or a measured distance between the distal end of the lithotripter and the impediment.

Another step 312 comprises activating the lithotripter to disrupt the structure of the impediment (e.g., stone) to form one or more fragments (e.g., stone fragments).

Another step 314 comprises introducing a wash fluid into the other cannula of the scope (i.e., the cannula that does not contain the lithotripter). Alternatively, a cannula that defines more than one lumen can be used. Therefore, the wash fluid can be introduced into the other lumen of the cannula (i.e., the lumen that does not contain the lithotripter). Any suitable wash fluid can be used, including saline and other wash and/or rinse fluids considered acceptable for use in medical procedures. It is noted that the step of introducing wash fluid can be conducted at any time during the method and for any duration. For example, in the case of sialendoscopy, the fluid is introduced from the beginning in order to dilate the duct and to aid in visualization. Optionally, the fluid is constantly injected during the entire time the scope is in place. For example, a step comprising continuing the step of introducing the wash fluid through the cannula until the wash fluid rises within the first lumen to a level sufficient for the suction force to pull the wash fluid into the second lumen can be performed while the step of activating the lithotripter to disrupt the structure of said impediment is being performed.

Another step 316 comprises continuing the step of applying a suction force until the wash fluid is drawn into the first fluid path and into the second lumen. This step is dependent on the method being conducted in a blind vessel, such as the salivary ducts. The blind nature of these vessels forces the wash fluid to re-enter the first lumen of the medical device as more fluid is introduced and the fluid seeks the path of least resistance. As the wash fluid re-enters the first lumen and, ultimately, enters the second lumen, the air flow from the external environment into the first lumen is blocked and the suction force begins drawing the wash fluid, and the fragments of the impediment, through the second lumen. The fragments and wash fluid can be collected as waste.

Various optional steps can be included, if desired. For example, to air in the removal of larger fragments of the impediment, another step 318 comprises removing the scope from the body vessel by withdrawing the cannulae through the first lumen of the pass-through fitting. Alternatively, a cannula that defines more than one lumen can be used. Therefore, step 318 can comprise removing the scope from the body vessel by withdrawing the cannula of the scope through the first lumen of the pass-through fitting such that the distal end of the scope is disposed proximal to the proximal opening of the first lumen. Following removal of the scope, another step 320 comprises introducing a catheter, such as a single lumen catheter, through the first lumen of the pass-through fitting and into the body vessel and then infusing wash fluid through the catheter, forcing fragments of the impediment up through the first lumen and then into the second lumen. At this point, relatively large fragments can exit the vessel by travelling through the lumen of the catheter. Following removal of the scope, another step 322 comprises continuing the step of applying a suction force until the wash fluid is drawn into the first fluid path and into the second lumen. Another optional step comprises removing the lithotripter from the body vessel by withdrawing the lithotripter from the scope through the cannula such that the distal end of the lithotripter is disposed proximal to the proximal end of the scope.

If additional disruption of the impediment is needed, steps 306 through 316 can be repeated a suitable number of times, with or without inclusion of the steps of removing the scope and introducing a catheter during each cycle.

It is also possible to use the single lumen catheter to flush fragments up through the first lumen and the stone fragments collect at the cap near the opening of the second lumen. In this case, the suction would be stopped and fluid injected from a port located at the valve on the second sheath. The valve is turned such that the suction is occluded and the side arm is in communication with the second lumen. Thus, when fluid is injected into the second sheath, it is passed back up the second lumen of the side arm, into the cap and into the first lumen of the main body to flush the stones out of the first lumen through the proximal opening. For example, referring to the medical device illustrated in the Figures, the suction may be occluded with valve 52 and fluid injected through an additional port located at valve 52 to travel through the second sheath lumen 46 and into the out proximal opening 36. This action moves impediments from the body of the sheath and the medical device 10. An alternative method to clear any fragments which may collect in the body of the sheath is to occlude suction with valve 52 and continue to infuse wash fluid through the irrigation catheter which forces flow through opening 36 which carries any impediments which collect at the body of the sheath out of the body of the sheath.

While various steps, alternative steps, and optional steps have been described above with respect to removing an impediment in a body vessel, these steps, alternative steps, and optional steps can be included in, accomplished concurrently with, and/or accomplished in the alternative to, the methodologies, steps, alternative steps, and/or optional steps described above with respect to the exemplary method 200 of removing an impediment in a body vessel.

Kits are also provided. An exemplary kit comprises a medical device according to an embodiment, such as the medical device 10 illustrated in FIG. 1; and any one or more of the following: a scope, such as scope 70 illustrated in FIG. 1; a scope having a cannula defining one or more lumens, a wire guide, a lithotripter, and an irrigation catheter. If included, the lithotripter can comprise any suitable lithotripter, such as a laser lithotripter, an ultrasonic lithotripter, and or pneumatic lithotripter. The lithotripter is sized and configured to be used with the medical device. As such, it includes a probe that is sized and configured to be capable of being passed into and substantially through the cannula of the scope.

In all embodiments, the medical device and, with kits, the components can be formed of any suitable materials and a skilled artisan will be able to select appropriate materials based on various considerations, such as a desired appearance, reuseability, and other considerations. The materials selected need only be considered safe for use in medical devices not intended for long term implantation. Examples of suitable materials include conventional plastic and metal materials commonly used in medical devices, and later-developed materials that become considered acceptable for such use.

The foregoing detailed description refers to exemplary occlusion devices and includes the best mode for practicing the invention. The description and the appended drawings illustrating the described devices are intended only to provide examples and not to limit the scope of the claims in any manner.

What is claimed is:
1. A medical device, comprising
a pass-through fitting defining a main body and a side arm, the main body having a proximal end, a distal end, and a first inner wall defining a first lumen extending along a first axis, the side arm having a second inner wall defining a second lumen in fluid communication with the first lumen and extending along a second axis disposed at an angle to the first axis, the first lumen having a proximal opening disposed at the proximal end of the main body and a distal opening disposed at the distal end of the main body;
a first sheath connected to the main body and in fluid communication with the first lumen;
a second sheath connected to the side arm and in fluid communication with the second lumen; and
a cannula having a proximal end and a distal end disposed through the first lumen proximal opening without blocking fluid flow into the first lumen proximal opening from the external environment such that the distal end of the cannula is disposed distal to the second lumen and a first fluid path is formed between the first inner wall and the cannula;
wherein a wash fluid passed through the proximal end of the cannula exits the distal end of the cannula; and
wherein a suction force applied to the second lumen pulls the wash fluid exiting the distal end of the cannula into the second lumen or pulls fluid from the external environment through the proximal opening of the first lumen and into the second lumen.

2. The medical device of claim 1, further comprising a valve attached to the second sheath and adapted to selectively permit and prevent the passage of fluid through the second lumen.

3. The medical device of claim 1, further comprising a proximal cap member attached to the main body, the proximal cap member defining a proximal cap member opening and a proximal cap member lumen that provides fluid access to the proximal opening of the first lumen.

4. The medical device of claim 1, wherein the first lumen has a proximal end disposed proximal to the second lumen and a distal end disposed distal to the second lumen;
wherein the proximal end has a first inner diameter;
wherein the distal end has a second inner diameter; and
wherein the first inner diameter is greater than the second inner diameter.

5. The medical device of claim 1, wherein cross-sectional area of the second lumen is equal to, substantially equal to, or greater than the cross-sectional area of the first lumen.

6. The medical device of claim 1, wherein the inner diameter of the second lumen is equal to, substantially equal to, or greater than the inner diameter of the first lumen.

7. The medical device of claim 1, wherein the first and second axes are coplanar.

8. The medical device of claim 7, wherein the angle is an angle between 0 degrees and 45 degrees.

9. The medical device of claim 7, wherein the angle is an angle between 45 degrees and 90 degrees.

10. The medical device of claim 7, wherein the angle is an angle between 135 degrees and 180 degrees.

11. The medical device of claim 7, wherein the angle is a 90 degree angle.

12. The medical device of claim 7, wherein the angle is a substantially 90 degree angle.

13. The medical device of claim 1, wherein the first sheath defines a flared first sheath proximal end.

14. The medical device of claim 13, further comprising a locking connector disposed over the flared first sheath proximal end to secure the first sheath to the pass-through fitting.

15. A medical device, comprising
a pass-through fitting defining a main body and a side arm, the main body having a proximal end, a distal end, and a first inner wall defining a first lumen extending along a first axis, the side arm having a second inner wall defining a second lumen in fluid communication with the first lumen and extending along a second axis disposed at an angle to the first axis, the first lumen having a first lumen proximal opening disposed at the proximal end of the main body, a first lumen distal opening disposed at the distal end of the main body, a first lumen first inner diameter at the first lumen proximal opening, and a first lumen second inner diameter at the first lumen distal opening, the first lumen first inner diameter greater than the first lumen second inner diameter;

a first sheath connected to the main body and in fluid communication with the first lumen;

a second sheath connected to the side arm and in fluid communication with the second lumen; and a cannula having a proximal end and a distal end disposed through the first lumen proximal opening without blocking fluid flow into the first lumen proximal opening from the external environment such that the distal end of the cannula is disposed distal to the second lumen and a first fluid path is formed between the first inner wall and the cannula;

wherein a wash fluid passed through the proximal end of the cannula exits the distal end of the cannula; and wherein a suction force applied to the second lumen pulls the wash fluid exiting the distal end of the cannula into the second lumen or pulls fluid from the external environment through the proximal opening of the first lumen and into the second lumen.

16. The medical device of claim 15, wherein cross-sectional area of the second lumen is equal to, substantially equal to, or greater than the cross-sectional area of the first lumen.

17. The medical device of claim 15, wherein the inner diameter of the second lumen is equal to, substantially equal to, or greater than the inner diameter of the first lumen.

18. The medical device of claim 15, wherein the first and second axes are coplanar.

19. The medical device of claim 18, wherein the angle is a 90 degree angle or a substantially 90 degree angle.

20. A medical device, comprising a pass-through fitting defining a main body and a side arm, the main body having a proximal end, a distal end, and a first inner wall defining a first lumen extending along a first axis, the side arm having a second inner wall defining a second lumen in fluid communication with the first lumen and extending along a second axis disposed at an angle to the first axis, the first lumen having a first lumen proximal opening disposed at the proximal end of the main body, a first lumen distal opening disposed at the distal end of the main body, a first lumen first inner diameter at the first lumen proximal opening, and a first lumen second inner diameter at the first lumen distal opening, the first lumen first inner diameter greater than the first lumen second inner diameter;

a first sheath connected to the main body and in fluid communication with the first lumen, the first sheath having a flared first sheath proximal end;

a second sheath connected to the side arm and in fluid communication with the second lumen;

a locking connector disposed over the flared first sheath proximal end to secure the first sheath to the pass-through fitting; and a cannula having a proximal end and a distal end disposed through the proximal opening of the first lumen without blocking fluid flow into the first lumen proximal opening from the external environment and such that the distal end of the cannula is disposed distal to the second lumen and a first fluid path is formed between the first inner wall and the cannula;

wherein a wash fluid passed through the proximal end of the cannula exits the distal end of the cannula; and wherein a suction force applied to the second lumen pulls the wash fluid exiting the distal end of the cannula into the second lumen or pulls fluid from the external environment through the proximal opening of the first lumen and into the second lumen.

* * * * *